(12) United States Patent
Huang et al.

(10) Patent No.: US 7,991,564 B2
(45) Date of Patent: *Aug. 2, 2011

(54) METHODS FOR HIGH THROUGHPUT GENOTYPING

(75) Inventors: Jing Huang, Sunnyvale, CA (US); Keith W. Jones, Sunnyvale, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/638,939

(22) Filed: Dec. 15, 2009

(65) Prior Publication Data

US 2010/0144542 A1 Jun. 10, 2010

Related U.S. Application Data

(63) Continuation of application No. 11/608,233, filed on Dec. 7, 2006, now Pat. No. 7,634,363.

(60) Provisional application No. 60/748,427, filed on Dec. 7, 2005.

(51) Int. Cl.
  G06F 19/00 (2011.01)
  G06F 15/00 (2006.01)
  C12Q 1/68 (2006.01)
(52) U.S. Cl. .................................. 702/20; 435/6; 700/1
(58) Field of Classification Search .......................... None
  See application file for complete search history.

(56) References Cited

U.S. PATENT DOCUMENTS

| | | |
|---|---|---|
| 5,143,854 A | 9/1992 | Pirrung et al. |
| 5,242,974 A | 9/1993 | Holmes |
| 5,252,743 A | 10/1993 | Barrett et al. |
| 5,324,633 A | 6/1994 | Fodor et al. |
| 5,384,261 A | 1/1995 | Winkler et al. |
| 5,405,783 A | 4/1995 | Pirrung et al. |
| 5,412,087 A | 5/1995 | McGall et al. |
| 5,424,186 A | 6/1995 | Fodor et al. |
| 5,451,683 A | 9/1995 | Barrett et al. |
| 5,482,867 A | 1/1996 | Barrett et al. |
| 5,491,074 A | 2/1996 | Aldwin et al. |
| 5,527,681 A | 6/1996 | Holmes |
| 5,541,061 A | 7/1996 | Fodor et al. |
| 5,547,839 A | 8/1996 | Dower et al. |
| 5,550,215 A | 8/1996 | Holmes |
| 5,571,639 A | 11/1996 | Hubbell et al. |
| 5,578,832 A | 11/1996 | Trulson et al. |
| 5,593,839 A | 1/1997 | Hubbell et al. |
| 5,624,711 A | 4/1997 | Sundberg et al. |
| 5,631,734 A | 5/1997 | Stern et al. |
| 5,795,716 A | 8/1998 | Chee |
| 5,800,992 A | 9/1998 | Fodor et al. |
| 5,831,070 A | 11/1998 | Pease et al. |
| 5,834,758 A | 11/1998 | Trulson et al. |
| 5,837,832 A | 11/1998 | Chee et al. |
| 5,856,092 A | 1/1999 | Dale et al. |
| 5,856,101 A | 1/1999 | Hubbell et al. |
| 5,858,659 A | 1/1999 | Sapolsky et al. |
| 5,871,928 A | 2/1999 | Fodor et al. |
| 5,889,165 A | 3/1999 | Fodor et al. |
| 5,902,723 A | 5/1999 | Dower et al. |
| 5,936,324 A | 8/1999 | Montagu |
| 5,959,098 A | 9/1999 | Goldberg et al. |
| 5,968,740 A | 10/1999 | Fodor et al. |
| 5,974,164 A | 10/1999 | Chee |
| 5,981,185 A | 11/1999 | Matson et al. |
| 5,981,956 A | 11/1999 | Stern |
| 6,013,449 A | 1/2000 | Hacia et al. |
| 6,020,135 A | 2/2000 | Levine et al. |
| 6,025,601 A | 2/2000 | Trulson et al. |
| 6,033,860 A | 3/2000 | Lockhart et al. |
| 6,040,138 A | 3/2000 | Lockhart et al. |
| 6,040,193 A | 3/2000 | Winkler et al. |
| 6,045,996 A | 4/2000 | Cronin et al. |
| 6,090,555 A | 7/2000 | Fiekowsky et al. |
| 6,136,269 A | 10/2000 | Winkler et al. |
| 6,141,096 A | 10/2000 | Stern et al. |
| 6,147,205 A | 11/2000 | McGall et al. |
| 6,177,248 B1 | 1/2001 | Oliner et al. |
| 6,185,030 B1 | 2/2001 | Overbeck |
| 6,197,506 B1 | 3/2001 | Fodor et al. |
| 6,201,639 B1 | 3/2001 | Overbeck |
| 6,218,803 B1 | 4/2001 | Montagu et al. |

(Continued)

FOREIGN PATENT DOCUMENTS

WO   WO 99/36760   7/1999

(Continued)

OTHER PUBLICATIONS

Hua et al. SNiPer-HD: improved genotype calling accuracy by an expectation-maximization algorithm for high-density SNP arrays Bioinformatics vol. 23, pp. 57-63 (2006).*
U.S. Appl. No. 09/536,841, filed Mar. 27, 2000, Fan et al.
U.S. Appl. No. 60/319,253, filed May 17, 2002, Dong et al.
U.S. Appl. No. 60/364,731, filed Mar. 15, 2002, Weiner et al.
U.S. Appl. No. 60/744,002, filed Mar. 30, 2006, Cawley et al.
AFFYMETRIX, BRLMM: An Improved Genotype Calling Method for the Genechip Human Mapping 500K Array set, revision date Apr. 14, 2006.

(Continued)

*Primary Examiner* — John S Brusca
(74) *Attorney, Agent, or Firm* — Sandra E. Wells

(57) ABSTRACT

Methods for genotyping polymorphisms using allele specific probes are disclosed. A training set is used to generate a model for each polymorphism to be interrogated. The training set is used to obtain an estimate of the asymmetry between an intensity measurement for a first allele and an intensity measurement for a second allele of the same polymorphism. The intensity measurement obtained for a test sample is adjusted using the estimate of asymmetry prior to using the intensity measurements to make a genotyping call. In preferred embodiments the adjustment is applied to polymorphisms that have a likelihood of being heterozygous that is above a specified threshold.

13 Claims, 2 Drawing Sheets

U.S. PATENT DOCUMENTS

| | | |
|---|---|---|
| 6,225,625 B1 | 5/2001 | Pirrung et al. |
| 6,262,216 B1 | 7/2001 | McGall |
| 6,269,846 B1 | 8/2001 | Overbeck et al. |
| 6,284,460 B1 | 9/2001 | Fodor et al. |
| 6,300,063 B1 | 10/2001 | Lipshutz et al. |
| 6,309,822 B1 | 10/2001 | Fodor et al. |
| 6,310,189 B1 | 10/2001 | Fodor et al. |
| 6,333,179 B1 | 12/2001 | Matsuzaki et al. |
| 6,361,947 B1 | 3/2002 | Dong et al. |
| 6,368,799 B1 | 4/2002 | Chee |
| 6,428,752 B1 | 8/2002 | Montagu |
| 6,872,529 B2 | 3/2005 | Su |
| 2005/0123971 A1 | 6/2005 | Di et al. |
| 2005/0164270 A1 | 7/2005 | Balaban et al. |
| 2005/0208555 A1 | 9/2005 | Raimond et al. |
| 2005/0222777 A1 | 10/2005 | Kaushikkar |
| 2005/0227244 A1 | 10/2005 | Matsuzaki et al. |
| 2005/0250151 A1 | 11/2005 | Mei et al. |
| 2005/0287575 A1 | 12/2005 | Di et al. |

FOREIGN PATENT DOCUMENTS

| | | |
|---|---|---|
| WO | WO 99/47964 | 9/1999 |
| WO | WO 00/58516 | 10/2000 |
| WO | WO01/58593 | 8/2001 |

OTHER PUBLICATIONS

Di et al, Bioinformatics 21:1958 21:1958-1963 (2005).
Fan et al, Cold Spring Harb. Symp. Quant. Biol. 68:69-78 (2003).
Fan et al, Genome Research 10:853-60 (2000).
Gunderson et al, Nat. Genet. 37, 549-554 (2005).
Hardenbol et al, Nature Biotech, 21:673-678 (2003).
Lovmar et al, Quantitative evaluation by minisequencing and microarrays reveals accurate multiplexed SNP genotyping if whole genome amplified DNA, Nucleic Acids Research vol. 31, paper e129, pp. 1-9 (2003).
Pastinen et al, Genome Research 10:1031 (2000).
Rabbee and Speed, Bioinformatics 22:7-12 (2006).
Synaven, Nat. Genet. Suppl: S5-10(2005).

* cited by examiner

METHODS FOR HIGH THROUGHPUT GENOTYPING

RELATED APPLICATIONS

This application is a continuation of U.S. patent application Ser. No. 11/608,233 filed Dec. 6, 2006, now U.S. Pat. No. 7,634,363, and claims priority to U.S. Provisional Patent Application No. 60/748,427 filed Dec. 7, 2005, the entire disclosures of which are incorporated herein by reference.

FIELD OF THE INVENTION

The invention is related to methods of genotyping polymorphisms. The present invention relates to computer systems, methods, and products for the analysis of microarray hybridization data.

BACKGROUND OF THE INVENTION

The genetic sequences of different individuals are identical over the majority of the genome and vary on average only at about one base in every 1000. The most common form of variation is a difference at a single base, known as a single nucleotide polymorphism or SNP. At these SNP positions some portion of the population will have one base while another portion of the population with have a different base. SNPs act as markers to locate regions of a genome that may be associated with a particular phenotype, such as a risk for disease.

SUMMARY OF THE INVENTION

Methods for calling the genotype of a sample at a selected polymorphism in a sample using a genotyping array are disclosed. In preferred aspects the methods include a normalization step where an intensity measurement for a first allele is adjusted to account for an asymmetry in intensity measurements between the first allele and a second allele that are observed in a training set of samples.

In one aspect the steps include: obtaining intensity measurements for allele A and for allele B for a plurality of polymorphisms in a plurality of training samples, wherein the genotype of each polymorphism in the plurality in each training sample is known of known genotype, wherein the intensity measurements represent intensity of signal associated with one or more features on said genotyping array, making a genotype call for each of a said polymorphisms in each of the training samples using the intensity measurements for allele A and for allele B obtained above, comparing the genotype call with the known genotype to identify individuals where the correct genotype call was made, using the intensity measurements from the individuals identified above to calculate a ratio of intensity measurement for allele A to intensity measurement for allele B, for the training samples for each subgroup of AA, AB and BB to obtain an AA reference ratio, an AB reference ratio and a BB reference ratio for each of said polymorphisms; hybridizing a test sample to the genotyping array to obtain hybridization intensity values for the A allele and for the B allele for each of said polymorphisms in the test sample; calculating a ratio of the intensity measurement for the A allele to the B allele for each of said polymorphisms in the test sample and compare the ratio to the reference ratios for AA, AB and BB obtained for that polymorphism above to determine the likelihood that the polymorphism is AB, identifying a subset of the polymorphisms in the test sample that are likely to be AB, wherein a polymorphism is identified as being likely to be AB if the likelihood that the polymorphism is AB is greater than a selected threshold, adjusting the intensity measurement of the B allele by the reference ratio for the AB group for that polymorphism from the training set to obtain an adjusted intensity measurement for the B allele, for each polymorphism in the subset of polymorphisms identified above; and generating a genotype call for each polymorphisms identified above using the use the adjusted intensity measurement for the B allele.

In one aspect, the allele specific intensity measurements may be measurements of the amount of target hybridized to an allele specific probe or set of probes. In another aspect, the allele specific intensity measurements may be measurements of the amount of signal incorporated into a probe in a template dependent primer extension assay such as a single base extension assay or an allele specific primer extension assay.

In another aspect computer software and systems to implement the disclosed methods are contemplated.

The above implementations are not necessarily inclusive or exclusive of each other and may be combined in any manner that is non-conflicting and otherwise possible, whether they are presented in association with a same, or a different, aspect of implementation. The description of one implementation is not intended to be limiting with respect to other implementations. Also, any one or more function, step, operation, or technique described elsewhere in this specification may, in alternative implementations, be combined with any one or more function, step, operation, or technique described in the summary. Thus, the above implementations are illustrative rather than limiting.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

(A) General

Figure 1:
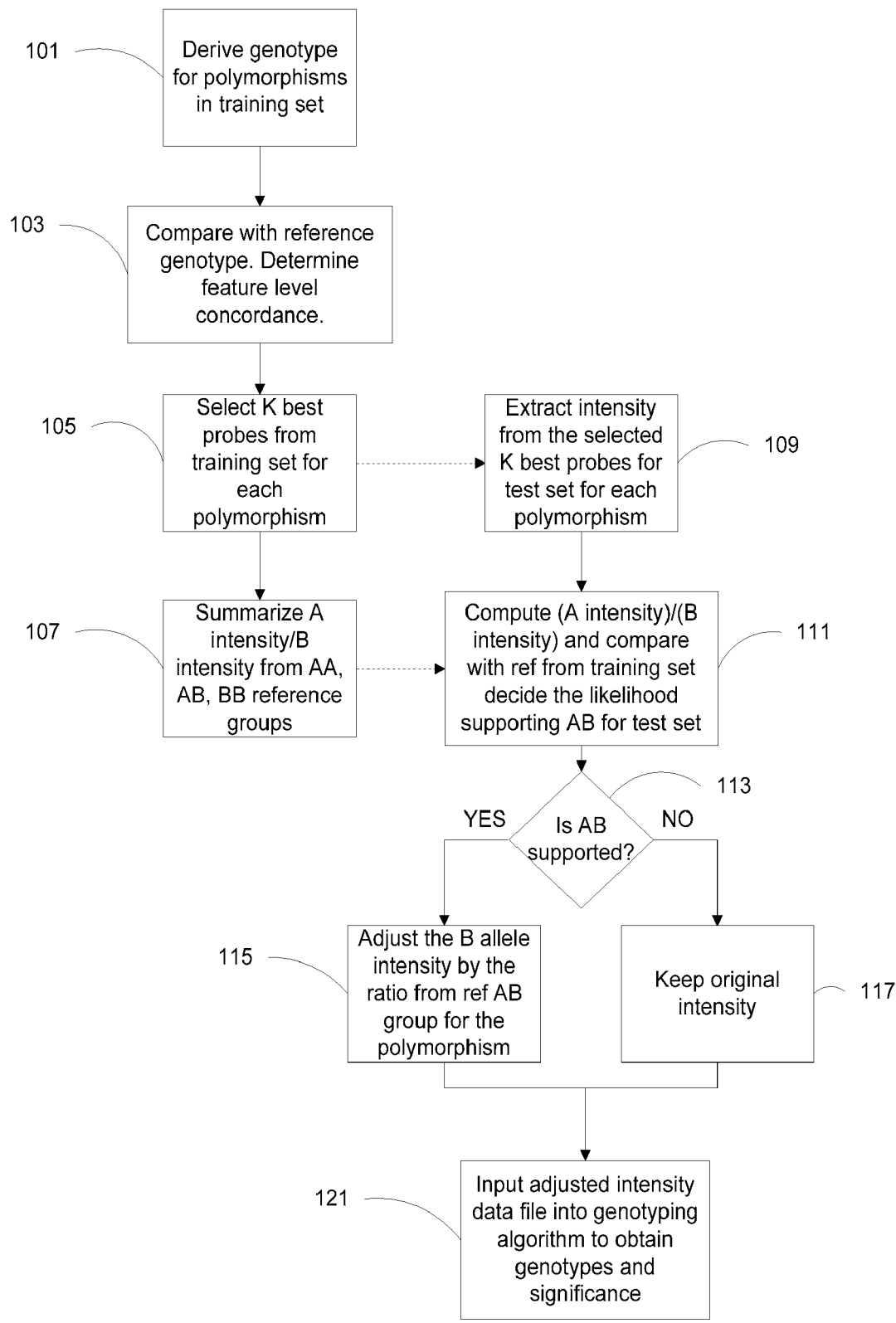
FIG. 1 is a flowchart for making heterozygous calls using intensity measurements from a training sample to adjust the intensity measurement for one allele.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. All references to the function log default to e as the base (natural log) unless stated otherwise (such as $\log_{10}$).

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, *Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159, 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al. 1992, Nucleic Acids Res. 20(7):1691-6, 1992, and rolling circle amplification, described in U.S. Pat. No. 5,648,245. Other amplification methods that may be used are described in, U.S. Pat. Nos. 5,242,794, 5,494,810, 4,988,617 and in U.S. Ser. No. 09/854,317 and US Pub. No. 20030143599, each of which is incorporated herein by reference. In some embodiments DNA is amplified by multiplex locus-specific PCR. In a preferred embodiment the DNA is amplified using adaptor-ligation and single primer PCR. Other available methods of amplification, such as balanced PCR (Makrigiorgos, et al. (2002), *Nat Biotechnol*, Vol. 20, pp. 936-9), may also be used.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. patent application Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S.*, 80: 1194 (1983). Methods and apparatus for carrying out repeated and controlled hybridization reactions have been described in U.S. Pat. Nos.

5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956; 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Computer methods related to genotyping using high density microarray analysis may also be used in the present methods, see, for example, US Patent Pub. Nos. 20050250151, 20050244883, 20050108197, 20050079536 and 20050042654.

Additionally, the present invention may have preferred embodiments that include methods for providing genetic information over networks such as the Internet as shown in U.S. patent application Ser. Nos. 10/063,559, 60/349,546, 60/376,003, 60/394,574, 60/403,381.

(B) Definitions

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry*, at 793-800 (Worth Pub. 1982) which is herein incorporated by its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

"Genome" designates or denotes the complete, single-copy set of genetic instructions for an organism as coded into the DNA of the organism. A genome may be multi-chromosomal such that the DNA is cellularly distributed among a plurality of individual chromosomes. For example, in human there are 22 pairs of chromosomes plus a gender associated XX or XY pair.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

An "array" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., *Science*, 251:767-777 (1991). Each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as optical fibers, glass or any other appropriate substrate. (See U.S. Pat. Nos. 5,770,358, 5,789,162, 5,708,153, 6,040,193 and 5,800,992, which are hereby incorporated by reference in their entirety for all purposes.)

Preferred arrays are commercially available from Affymetrix under the brand name GENECHIP® and are directed to a variety of purposes, including genotyping and gene expression monitoring for a variety of eukaryotic and prokaryotic species. (See Affymetrix Inc., Santa Clara and their website at affymetrix.com.) Methods for preparing sample for hybridization to an array and conditions for hybridization are disclosed in the manuals provided with the arrays, for example, for expression arrays the GENECHIP Expression Analysis Technical Manual (PN 701021 Rev. 5) provides detailed instructions for 3' based assays and the GeneChip® Whole Transcript (WT) Sense Target Labeling Assay Manual (PN 701880 Rev. 2) provides whole transcript based assays. The GeneChip Mapping 100K Assay Manual (PN 701694 Rev. 3) provides detailed instructions for sample preparation, hybridization and analysis using genotyping arrays. In preferred aspects the arrays may be the Mapping 10K, Mapping 100K or Mapping 500K arrays or array sets.

In another aspect arrays that may be used in connection with the methods include bead arrays such as those described in Gunderson et al., *Genome Res.* 14:870-877 (2004). The methods may be applied to a variety of genotyping methods, including, for example, those described in Fan et al., *Nat. Rev. Genet.* 7:632 (2006) and Fan et al. *Methods Enzymol.* 410: 57-73 (2006).

In another aspect the methods may be applied to genotyping assays that use a universal array for detection. Such methods include, for example, the Molecular Inversion Probe (MIP) assay and the GoldenGate assay. See, Hardenbol et al., *Nature Biotech.* 21:673-678 (2003) and Fan et al., *Cold Spring Harb. Symp. Quant. Biol.* 68:69-78 (2003).

An allele refers to one specific form of a genetic sequence (such as a gene) within a cell, a sample, an individual or within a population, the specific form differing from other forms of the same gene in the sequence of at least one, and frequently more than one, variant sites within the sequence of the gene. The sequences at these variant sites that differ between different alleles are termed "variants", "polymorphisms", or "mutations". In general, polymorphism is used to refer to variants that have a frequency of at least 1% in a population, while the term mutation is generally used for variants that occur at a frequency of less than 1% in a population. In diploid organisms such as humans, at each autosomal specific chromosomal location or "locus" an individual possesses two alleles, a first inherited from one parent and a second inherited from the other parent, for example one from the mother and one from the father. An individual is "heterozygous" at a locus if it has two different alleles at the locus. An individual is "homozygous" at a locus if it has two identical alleles at that locus.

Preferred markers have at least two alleles, each occurring at frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. The most frequent allele may also be referred the major allele and the less frequent allele as the minor allele. Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens. Single nucleotide polymorphisms (SNPs) are positions at which two alternative bases occur at appreciable frequency (>1%) in the human population, and are the most common type of human genetic variation.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be a T in some individuals and a C in other individuals. Those individuals who have a T at the position have the T allele and those who have a C have the C allele. In a diploid organism the individual will have two copies of the sequence containing the polymorphic position so the individual may have a T allele and a C allele or alternatively two copies of the T allele or two copies of the C allele. Those individuals who have two copies of the C allele are homozygous for the C allele, those individuals who have two copies of the T allele are homozygous for the T allele, and those individuals who have one copy of each allele are heterozygous. The alleles are often referred to as the A allele, often the major allele, and the B allele, often the minor allele. The genotypes may be AA (homozygous A), BB (homozygous B) or AB (heterozygous). Genotyping methods generally provide for identification of the sample as AA, BB or AB.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles A and B, which occur at equal frequency, and linked locus Y has alleles C and D, which occur at equal frequency, one would expect the combination AC to occur at a frequency of 0.25. If AC occurs more frequently, then alleles A and C are in linkage disequilibrium. Linkage disequilibrium (or LD) may result, for example, because the regions are physically close, from natural selection of certain combination of alleles or because an allele has been introduced into a population too recently to have reached equilibrium with linked alleles.

A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable. Studies using panels of human SNPs to identify evidence for linkage between genomic regions and disease phenotypes have been described. See, for example, Boyles et al., *Am J Med Genet A.* 140(24):2776-85 (2006), Klein et al. Science 308: 385 (2005), Papassotiropoulos et al., *Science* 314:475-478 (2006), Craig and Stephan, *Expert Rev Mol Diagn* 5(2):159-70 (2005) and Puffenberger et al., *PNAS* 101:11689-94 (2004).

Normal cells that are heterozygous at one or more loci may give rise to tumor cells that are homozygous at those loci. This loss of heterozygosity may result from structural deletion of normal genes or loss of the chromosome carrying the normal gene, mitotic recombination between normal and mutant genes, followed by formation of daughter cells homozygous for deleted or inactivated (mutant) genes; or loss of the chromosome with the normal gene and duplication of the chromosome with the deleted or inactivated (mutant) gene.

A homozygous deletion is a deletion of both copies of a gene or of a genomic region. Diploid organisms generally have two copies of each autosomal chromosome and therefore have two copies of any selected genomic region. If both copies of a genomic region are absent the cell or sample has a homozygous deletion of that region. Similarly, a hemizygous deletion is a deletion of one copy of a gene or of a genomic region.

Genetic rearrangement occurs when errors occur in DNA replication and cross over occurs between nonhomologous regions resulting in genetic material moving from one chromosomal location to another. Rearrangement may result in altered expression of the genes near the rearrangement.

An aneuploid is a cell whose chromosomal constitution has changed from the true diploid, for example, extra copies of a chromosome or chromosomal region.

An individual is not limited to a human being, but may also include other organisms including but not limited to mammals, plants, bacteria or cells derived from any of the above.

In some aspects information about one SNP may be used to extrapolate to information about another SNP that is part of a haplotype. Information about haplotypes, uses of haplotypes and methods of haplotype analysis are described, for example, in de Bakker et al., *Nature Genet.* 37:1217-1223 (2005), Goldstein and Cavalleri, *Nature* 437:1241-1242 (2005), Wang et al., *Nat. Rev. Genet.* 6:109-118 (2005), Carlson et al., *Nature* 429:446-452 (2004) and Clayton et al., *Nature Genet.* 37:1243-46 (2005).

The Whole Genome Sampling Assay (WGSA) reduces the complexity of a nucleic acid sample by amplifying a subset of the fragments in the sample. A nucleic acid sample is fragmented with one or more restriction enzymes and an adapter is ligated to both ends of the fragments. A primer that is complementary to the adapter sequence is used to amplify the fragments using PCR. During PCR fragments of a selected size range are selectively amplified. The size range may be, for example, 400-800 or 400 to 2000 base pairs. Fragments that are outside the selected size range are not efficiently amplified.

The fragments that are amplified by WGSA may be predicted by in silico digestion and an array may be designed to genotype SNPs that are predicted to be amplified. Genotyping may be done by allele specific hybridization with probes that are perfectly complementary to individual alleles of a SNP. A set of probes that are complementary to the region surrounding each SNP may be present on the array. Perfect match probes are complementary to the target over the entire length of the probe. Mismatch probes are identical to PM probes except for a single mismatch base. The mismatch position is typically the central position so for a 25 base probe the mismatch is position 13.

The methods may be combined with other methods of genome analysis and complexity reduction. Other methods of complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592, 6,458, 530 and U.S. Patent application Nos. 20030039069, Ser. Nos. 09/916,135, 09/920,491, 09/910,292 and 10/264,945, which are incorporated herein by reference in their entireties.

The design and use of allele-specific probes for analyzing polymorphisms is described by e.g., Saiki et al., *Nature* 324, 163-166 (1986); Dattagupta, EP 235,726, Saiki, and WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles.

(C) Methods for Genotyping Heterozygous Loci

For biallelic polymorphisms in diploid organisms (with alleles A or B) there are generally three available genotype calls, AA, BB or AB. The AB call, or the heterozygous call, is often the most difficult to make and often results in a "no call" being made. A "no call" result is often the result of the genotyping software making a call that is below a user defined threshold of reliability. Methods are disclosed herein for improved methods for making heterozygous genotyping calls from intensity data obtained from probe arrays. In general, the methods involve a normalization step for the intensity measurement obtained for one of the two alleles, using an adjustment factor calculated from intensities observed in a training set of samples of known genotype. Often there is an asymmetry observed between the intensity measurement obtained for the two alleles and adjusting for the asymmetry can improve the ability to call heterozygotes. The asymmetry may be the result, for example, of differences in hybridization kinetics between the target and the allele specific probes for each of the different alleles. In some aspects the probes may vary only at the interrogation position (the base complementary to the polymorphic position) but in others they may have additional differences. In assays based on enzymatic discrimination, the differences may be the result of differences in enzyme kinetics for different bases. In some aspects the scale of asymmetry is estimated and used to adjust the intensity measurement values for one of the alleles to normalize for the asymmetry.

In a preferred aspect, the method takes into consideration the observation that the intensity measurement for the A allele and the intensity measurement for the B allele may vary significantly despite approximately equal amounts of the two alleles in the starting material. For example, the A allele may have an intensity measurement of about 10,000 and the B allele may have an intensity measurement of about 6,000. This may result in a no-call because the variation is greater than expected. In the methods disclosed herein a training set of samples of known genotype are used to derive a normalization factor for this SNP. For example, the training set of individuals of known genotype at the SNP are interrogated to obtain intensity measurements for the A and B alleles and the measurements are averaged in an allele specific manner to obtain and average intensity for the A allele and an average intensity for the B allele, which may be, for example, 10,000 and 5,000. A ratio of the A average to the B average may be calculated (10,000/5,000=2 in this example) and the measurement for B in the unknown sample may be normalized using this number (6,000×2=12,000) and the normalized measurement used to make the genotyping call. In this example, the adjusted measurement for B is 12,000 and the unadjusted measurement for A is 10,000 and because the numbers fit the algorithm model for a heterozygout, a heterozygous call is made.

Methods for calling the genotype of a biological sequence using data obtained from a microarray are disclosed herein. The methods are related to those disclosed in US Patent Publication Nos. 20050287575 and 20050123971, which are incorporated herein by reference in their entireties. In particular, US Patent Publication No. 20050123971 discloses methods for calling the genotype of a sample using a dynamic modeling algorithm.

One of the challenges of genotyping diploid organisms is that heterozygous loci (AB) are often more difficult to accurately genotype than homozygous loci (AA or BB). Differences in hybridization behavior of the allele specific probes for the different alleles may account for some of this difficulty. Methods for making genotype calls may be biased against making calls for heterozygous loci and may generate "no calls" frequently because the algorithms assume that the intensities or signal from the A allele probes and the intensities or signal from the B allele probes should be similar and share the same distribution. The methods disclosed employ an intensity transformation procedure performed prior to the Dynamic Modeling (DM) algorithm to address asymmetry between the A and B allele probes.

In one embodiment the distribution of PMa/PMb for the reference quartets is compared to the PMa/PMb for the experimental sample and a P value is obtained for each possible genotype. If the P value for the AB call is at least 0.4 the AB call is supported and the PMb intensity value is adjusted. The difference between the P value for AB should vary from the next highest P value by at least 0.2. For example, if the P value for the AB call is 0.8, for AA is 0.0035 and for BB is 0.015 the AB call is supported.

For the training set, the algorithm employs a quartet selection step and an intensity-ratio summarization step. In the quartet selection step, a fixed number of quartets are selected based on their quartet level concordance derived by comparison with the reference genotype. The quartet level genotype is calculated using the DM algorithm. In the ratio summarization step, PMa/PMb intensity ratio distribution is summarized for AA, AB and BB sub-groups. This summarization requires that there are at least two samples for each genotype at that particular SNP. For SNPs that do not meet this criterion, only the quartet selection step is carried out, but no intensity adjustment step on the test set thereafter.

For the test set, the algorithm consists of a feature extraction step, an evaluation step of whether a selected quartet supports a heterozygous call, and an intensity adjustment step. In the feature extraction step, only the intensity measures from the k selected quartets (determined by the training set) is obtained and further used. In the evaluation step, the PMa/PMb ratios from the selected quartets are compared against the corresponding distribution derived from the training set. Only those that show a strong possibility of supporting a heterozygous call are further selected for intensity adjustment. Intensity adjustment is done by multiply the mean and standard deviation of the PMb feature intensity by the mean PMa/PMb ratio of the reference sub-group that calls "AB" on that particular SNP. In one embodiment, the quartets are selected as supporting a heterozygous call if the PMa/PMb ratio from the test sample is compared with the reference distribution from AA, AB and BB groups and the p-value from the comparison with the AB group is the largest and exceeds 0.4 and the difference between this p-value and the second largest p-value is greater than 0.2.

After the quartet selection and intensity adjustment, DM is applied on this transformed intensity set and genotypes and significance are recalculated. In the experiments using whole genome target, we observe substantial improvement in the genotyping quality after this intensity adjustment. The improvement is especially significant on heterozygous calls.

FIG. 1 shows a schematic of the method. In step [101] a genotype is derived from a training set using the genotyping algorithm. The genotype from [101] is compared with the reference genotype to obtain feature level concordance for the training set [103]. The best features are selected from the training set based on concordance [105]. The (A intensity)/(B intensity) distribution from AA, AB and BB sub-groups in the training set are summarized [107]. Intensities are extracted from the selected K best features for the test set [109]. The (A intensity)/(B intensity) for the test set is compared with the reference from the training set to decide the likelihood of supporting AB call for the test set [111]. If AB is supported the B allele intensity is adjusted by the ratio from the reference AB group [115]. If AB is not supported the original intensity for both A and B is maintained [117]. The intensity values are fed back into a genotyping algorithm to get genotype and significance [121]. Steps 101, 103, 105 and 107 are performed on the training set. Steps 109, 111, 113, 115, 117 and 121 are performed on the test set. The genotypes of the training set are known. The genotypes of the test set are unknown.

Figure 2:
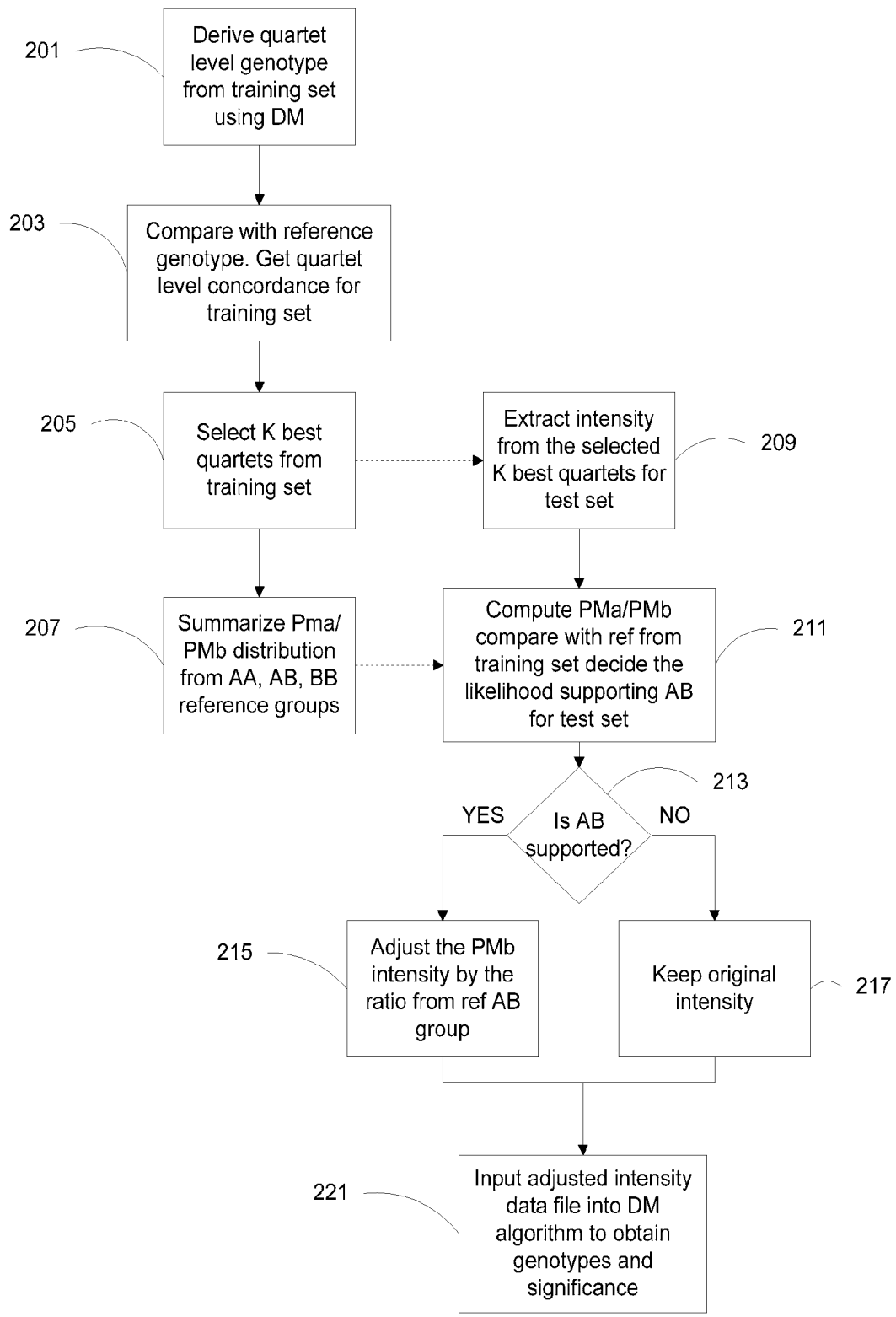
FIG. 2 is a flowchart of an embodiment using hybridization intensities from allele specific probes.

FIG. 2 shows a schematic of an embodiment of the method as applied to a genotyping array using allele specific probes. The intensities are hybridization intensities that measure the amount of a labeled target that is hybridized to individual probe features. In step [201] a quartet level genotype is derived from a training set using the DM algorithm. The genotype from [201] is compared with the reference genotype to obtain a quartet level concordance for the training set [203]. The best quartets are selected from the training set based on concordance [205]. The PMa/PMb distribution from AA, AB and BB sub-groups in the training set are summarized [207]. Intensities are extracted from the selected K best quartets for the test set [209]. PMa/PMb for the training set is compared with the reference from the training set to decide the likelihood of supporting AB call for the test set [211]. If AB is supported the PMb intensity is adjusted by the ratio from the reference AB group [215]. If AB is not supported the original intensity is maintained [217]. The intensity values are feed back into DM to get genotype and significance [221]. Steps 101, 103, 105 and 107 are performed on the training set. Steps 209, 211, 213, 215, 217 and 221 are performed on the test set. The genotypes of the training set are known. The genotypes of the test set are unknown.

FIG. 2. Each individual in the training set is evaluated at the quartet level to get a predicted genotype for each SNP for each individual. The genotypes are compared to the reference genotype to obtain a concordance measure for each SNP in the training set. For a given SNP the K quartets with the highest concordance are selected for further analysis. In a preferred aspect K is a constant and may be, for example, 3, 4, 5, 6, or 7. K is less than the total number of quartets and represents a high performing subset of quartets for a given SNP. In another embodiment K may vary from SNP to SNP and may be determined by a threshold concordance, for example, all quartets that have a concordance between the reference genotype and the predicted quartet level genotype within the reference set, may be selected. Summarize the distribution of PMa/PMb for the selected quartets for each SNP and each of the three genotypes, AA, AB and BB for the reference set. So for each SNP you have a selected set of the K best quartets and for each quartet a mean and standard deviation for each of the three genotypes based on the reference set of samples. For the unknown sample intensity information is extracted from the K best quartets for each SNP. PMa/PMb is calculated for each quartet and compared to the PMa/PMb values obtained for that quartet in the reference set for AA, AB or BB reference genotypes. The experimental PMa/PMb value is compared to the PMa/PMb value for the AB, AA and BB genotypes to determine if an AB call is supported. This is done at the quartet level and the reference genotype level. The AB call is supported if the ratio from the experimental sample is closer to the AB value than to the AA or BB value by at least a minimum threshold. If the AB call is supported, the PMb intensity is adjusted by multiplying the PMb intensity value by the PMa/PMb value from the AB reference set for the genotype. If the AB call is not supported no adjustment to the PMb value is made. After the adjustment step the intensities are used to make genotyping calls using the DM algorithm (Di et al., *Bioinformatics* 21:1958-1963 (2005). Other algorithms may be used, for example, Hua et al., bioinformatics 2006 (PMID 17062589) discloses an expectation-maximization algorithm for use with high density SNP arrays, Rabbee and Speed Bioinformatics 22:7-12 (2006) discloses the RLMM algorithm as applied to SNP arrays, this is a robustly fitted, linear model that uses the Mahalanobis distance for classification. In another embodiment the algorithm is based on BRLMM as described in BRLMM: an Improved Genotype Calling Method for the GeneChip Human Mapping 500K Array set, white paper available at Affymetrix web site, revision date 2006-04-14, see also, U.S. Provisional Patent application No. 60/744,002 filed Mar. 30, 2006.

Related methods of analysis of genotype information are also disclosed in U.S. Patent Publication Nos. 20050287575, 20050250151, 20050227244, 20050222777, 20050208555, and 20050164270.

Also, each embodiment of probe array may include a plurality of probe sets each comprising a plurality of probes enabled to interrogate the nucleotide composition of each SNP position. Also, some embodiments include one or more probe sets enabled to interrogate sequence composition associated with a complementary sequence (i.e. complementary sequence by Watson-Crick base paring rules) region on each of the two strands of DNA, for example, the sense strand and the anti-sense strand of DNA.

In another aspect, the methods may be applied to a genotyping system that uses single base extension (SBE) or allele specific primer extension (ASPE). SBE has been described, for example, in Fan et al., Genome Res. 10:853-60 (2000). For SBE, a single locus specific primer that hybridizes immediately adjacent to the polymorphism is extended with a base that is complementary to the polymorphic base. The base that is added is identified to identify which allele of the polymorphism is present. For ASPE, each allele of the polymorphisms is targeted by a different allele specific probe. The probe hybridizes to the region of the target including the polymorphism and is extended to incorporate labeled nucleotides. ASPE has been described, for example, in Patinen et al., Genome Res. 10:1031 (2000). ASPE methods for genotyping using arrays of probes attached to beads have been described, for example, in Gunderson et al *Nat. Genet.* 37, 549-554 (2005). For a description of other SNP genotyping methods to which the disclosed methods may be applied see Syvanen, *Nat. Genet. Suppl*: S5-10 (2005).

In one aspect each SNP is interrogated by a probe set that includes one or more probe quartets. Each probe quartet is comprised of a Perfect Match (PM) and a Mismatch (MM) probe for each allele. The probes of a quartet are complementary to the same strand (sense or antisense) but different quartets may be complementary to different strands. A probe set may include one or more quartets to the sense strand and one or more quartets to the antisense strand. In a preferred aspect the probe set for each SNP includes 7 to 10 probe quartets. Preferably the oligonucleotides of a quartet are 20 to 50 bases, more preferably 20-30 bases and most preferably 25 bases in length. Each probe is located in a different feature of the array and there are multiple copies of the probe in the feature, preferably more than 1 million copies of the probe in that probe's feature. The array may have more than 1 million and preferably more than 2.5 million features. In preferred aspects the array contains probe sets for more than 50,000 different SNPs. Exemplary arrays include the Affymetrix Mapping 100K array set. See Data Sheet GeneChip® Human Mapping 100K Set available from Affymetrix (PN 701674 Rev. 3) and the Mapping 100K Assay Manual.

In a preferred aspect, genomic material is hybridized to arrays without reduction of complexity. These whole genome hybridization experiments make genotype calling more difficult. In one example, different stringencies of washes were used. For the test set the wash was in 0.6×SSPE (90 mM NaCl, 6 mM NaH2Po4) and the training set was washed in 50 mM Tris pH 8.3 with varying salt concentrations of either 75 mM, 100 mM, or 125 mM NaCl. The samples tested were 16 HapMap samples and 150 μg of whole genome target was hybridized to the arrays. Hybridization was at 50° C. for 18 hours in 0.6×SSPE. The results showed that there was an increased asymmetry between PMa and PMb intensity and adjusting to minimize the asymmetry improved heterozygous call efficiency.

CONCLUSION

Methods of determining genotypes of polymorphisms are disclosed. All cited patents, patent publications and references are incorporated herein by reference for all purposes.

It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring signal intensity resulting from genomic DNA could be used. The scope of the invention should, therefore, be determined not with reference to the above description, but should instead be determined with reference to the appended claims, along with the full scope of equivalents to which such claims are entitled.

What is claimed is:

1. A method for calling the genotype of a sample at a selected polymorphism in a sample using a genotyping array, comprising:

(a) obtaining intensity measurements for allele A and for allele B for a plurality of polymorphisms in a plurality of training samples, wherein the genotype of each polymorphism in the plurality in each training sample is known, wherein the intensity measurements represent intensity of signal associated with one or more features on said genotyping array;

(b) making a genotype call for each of a said polymorphisms in each of the training samples using the intensity measurements for allele A and for allele B obtained in (a);

(c) comparing the genotype call with the known genotype to identify individuals where the correct genotype call was made;

(d) using the intensity measurements from the individuals identified in (c) to calculate a ratio of intensity measurement for allele A to intensity measurement for allele B, for the training samples for each sub-group of AA, AB and BB to obtain an AA reference ratio, an AB reference ratio and a BB reference ratio for each of said polymorphisms;

(e) hybridizing a test sample to a second copy of the genotyping array to obtain hybridization intensity values for the A allele and for the B allele for each of said polymorphisms in the test sample;

(f) calculating a ratio of the intensity measurement for the A allele to the B allele for each of said polymorphisms in the test sample and comparing the ratio to the reference ratios for AA, AB and BB obtained for that polymorphism in (d) to obtain a p-value that the polymorphism is either AA, AB, or BB;

(g) identifying a subset of the polymorphisms in the test sample that are likely to be AB, wherein a polymorphism is identified as being likely to be AB if the p-value that the polymorphism is AB is greater than 0.4;

(h) adjusting the intensity measurement of the B allele by the reference ratio for the AB group for that polymorphism from the training set to obtain an adjusted intensity measurement for the B allele, for each polymorphism in the subset of polymorphisms identified in (g); and (i) generating a genotype call for each polymorphisms identified in (g) using the adjusted intensity measurement for the B allele.

2. The method of claim 1 wherein said polymorphisms are single nucleotide polymorphisms.

3. The method of claim 1 wherein said intensity measurement is obtained by measuring the amount of a labeled target that is hybridized to one or more allele specific probes.

4. The method of claim 1 wherein said intensity measurement is obtained by measuring the amount of label incorporated by extending a probe with one or more labeled nucleotides.

5. The method of claim 4 wherein the probe is extended enzymatically in a template dependent manner.

6. A system for calling the genotype of a sample using the method of claim 1, comprising:
    a scanner that generates allele specific intensity measurements for one or more polymorphisms from an array of probes; and
    a computer comprising system memory with executable code stored thereon, wherein the executable code is enabled to perform one or more of the steps of claim 1.

7. A method for genotyping a polymorphism in a test individual comprising:
    (a) obtaining allele specific intensity measurements for a first allele of the polymorphism and for a second allele of the polymorphism in a training set comprising a plurality of individuals of known genotype for said polymorphism;
    (b) grouping the individuals in the training set into groups according to genotype, wherein each individual is assigned to one of the following groups: homozygous for the first allele, homozygous for the second allele or heterozygous;
    (c) calculating a summary ratio of the intensity measurements for said first allele to the intensity measurements for said second allele for each group to obtain a first summary ratio for the group that are homozygous for said first allele, a second summary ratio for the group that are homozygous for said second allele and a third summary ratio for the group that are heterozygous;
    (d) obtaining an allele specific intensity for said first allele and for said second allele in said test individual and calculating a test ratio for said test individual;
    (e) adjusting the allele specific intensity value for said first allele according to the third summary ratio obtained in (c) if said test ratio is closer to the third summary ratio than to the first or second summary ratios; and
    (e) making a genotype call for said polymorphism using the adjusted value obtained in (e) for said first allele and the intensity value obtained in (d) for the second allele, wherein steps (b), (c) and (e) are performed by a computer and wherein the computer outputs the genotype call for said polymorphism in a readable format.

8. The method of claim 7 wherein the genotype call of step (e) is made using a dynamic modeling algorithm.

9. A method for calling the genotype of a sample at a selected polymorphism in a sample using a genotyping array, comprising:
    (a) obtaining hybridization intensity values for said genotyping array for each of a set of training samples comprising a plurality of training samples of known genotype;
    (b) making a genotype call for each of a plurality of SNPs in the each of the training samples using the hybridization intensity values from individual probe quartets;
    (c) comparing the genotype call with the known genotype for each probe quartet to identify a plurality of K best probe quartets for each SNP, where K is at least 1, wherein probe quartets are selected as best probe quartets if the genotype call made using said quartet has high concordance with the known genotype for that SNP;
    (d) calculating a distribution of (intensity A)/(intensity B) distribution for the training samples for each sub-group of AA, AB and BB to obtain an AA reference distribution, an AB reference distribution and a BB reference distribution;
    (e) hybridizing a test sample to the genotyping array to obtain hybridization intensity values for said K best probe quartets for the selected polymorphism;
    calculating (intensity A)/(intensity B) for each of the K best probe quartets for the selected polymorphism to obtain a ratio value for each and comparing each ratio value with the AA reference distribution, the AB reference distribution and the BB reference distribution for the polymorphism to obtain a p-value that the selected polymorphism is AB;
    (g) adjusting the intensity of intensity B by the (intensity A)/(intensity B) ratio from the AB group from the reference set to obtain an adjusted allele B intensity if the p-value that the selected polymorphism is AB is greater than 0.4; and
    (h) the adjusted intensity B value to generate a genotype call for the selected polymorphism using a selected algorithm.

10. The method of claim 9 wherein K is selected from 2, 3, 4, 5, 6 or 7.

11. The method of claim 10 wherein K is the same for each SNP in the plurality.

12. The method of claim 9 wherein K is selected for each SNP and is the number of quartets for that SNP that predict the correct genotype in the training set with a minimum concordance.

13. The method of claim 9 wherein the selected algorithm is a dynamic modeling algorithm.

* * * * *